US005193527A

United States Patent [19]

Schäfer

[11] Patent Number: 5,193,527

[45] Date of Patent: Mar. 16, 1993

[54] ULTRASONIC SHOCK-WAVE TRANSDUCER

[75] Inventor: Dagobert Schäfer, Bretten, Fed. Rep. of Germany

[73] Assignee: Richard Wolf GmbH, Knittlingen, Fed. Rep. of Germany

[21] Appl. No.: 580,226

[22] Filed: Sep. 10, 1990

[30] Foreign Application Priority Data

Oct. 3, 1989 [DE] Fed. Rep. of Germany ....... 3932967

[51] Int. Cl.[5] ............ A61B 17/22

[52] U.S. Cl. ............ 128/24 EL; 73/642; 310/335; 367/157

[58] Field of Search ........ 128/24 AA, 24 EL, 660.03, 128/662.03, 660.01; 73/642, 644; 310/369-371; 606/128; 367/157

[56] References Cited

U.S. PATENT DOCUMENTS

| | | | |
|---|---|---|---|
| 3,866,711 | 2/1975 | Folds | 181/176 |
| 4,029,395 | 6/1977 | Hurwitz et al. | 350/178 |
| 4,401,910 | 8/1983 | Beerman | 310/369 |
| 4,526,168 | 7/1985 | Hassler et al. | 128/303 R |
| 4,586,512 | 5/1986 | Do-huu et al. | 128/661.01 |
| 4,639,904 | 1/1987 | Riedlinger | 367/140 |
| 4,705,026 | 11/1987 | Chaussy et al. | 128/24 A |
| 4,771,787 | 9/1988 | Wirster et al. | 128/660.03 |
| 4,960,107 | 10/1990 | Aida et al. | 606/128 X |
| 4,961,176 | 10/1990 | Tanaka et al. | 128/660.01 |
| 5,050,588 | 9/1991 | Grey et al. | 128/24 EL |
| 5,111,805 | 5/1992 | Jaggy et al. | 128/24 EL |

FOREIGN PATENT DOCUMENTS

| | | |
|---|---|---|
| 0367117 | 5/1990 | European Pat. Off. . |
| 3119295 | 12/1982 | Fed. Rep. of Germany . |
| 3150513 | 6/1983 | Fed. Rep. of Germany . |
| 3417985 | 11/1985 | Fed. Rep. of Germany . |
| 3510341 | 10/1986 | Fed. Rep. of Germany . |
| 2126901 | 4/1984 | United Kingdom . |

OTHER PUBLICATIONS

Eisenberger et al., *Urologische Steintherapie*, 1987, pp. 26-27.

F. Ueberle, "Piezoelektrisch erzeugte Hochenergiepulse etc.," 1987.

*Primary Examiner*—Lee S. Cohen
*Assistant Examiner*—K. M. Pfaffle
*Attorney, Agent, or Firm*—Panitch, Schwarze, Jacobs & Nadel

[57] ABSTRACT

There is disclosed an ultrasonic shockwave transducer for use in lithotripsy, hypothermia and like treatments for generating ultrasonic shock waves and transmitting them to a concretion or tissue to be destroyed. The transducer is arranged to focus the energy of the ultrasonic shock waves proportionally onto at least two points disposed on a line disposed about the main axis of, and being spaced from the radiation surface of, the transducer, the line being arbitrarily curved in three dimensions.

8 Claims, 8 Drawing Sheets

ULTRASONIC SHOCK-WAVE TRANSDUCER

FIELD OF THE INVENTION

The invention relates to an ultrasonic shock-wave transducer for use in lithotripsy, hypothermia and like treatments, for generating ultrasonic shock waves and transmitting them to an object in the form of a concretion or tissue to be destroyed.

BACKGROUND OF THE INVENTION

Such a transducer is described in DE-A-3 510 341 (U.S. Pat. No. 4,639,904).

Cup-shaped or planar transducers as described in DE-A-3 119 295 (U.S. Pat. No. 4,526,168), in which the ultrasonic shock waves are focussed by electronic or acoustic means, are used in medicine for disintegrating concretions in body cavities, or for destroying tissue and the like.

In such transducers, it is always attempted to concentrate the ultrasonic shock waves most accurately at a geometrical or acoustic site or focus, in order to obtain the necessary energy density for the treatment in hand. For the application of the ultrasonic shock waves, said focus of the transducer is centered on the object to be destroyed.

Such ultrasonic shock waves are usually satisfactory when they are first applied. For example, there is a high probability of a sufficiently large concretion being destroyed when it is first treated. Frequently, however, a number of smaller fragments of the concretion are left and these in turn must be destroyed, at considerable expense, since each fragment must be individually treated.

SUMMARY OF THE INVENTION

An object of the invention is to provide an ultrasonic shock wave transducer in which the accuracy of aiming the ultrasonic shock waves is improved, more particularly for the more rapid destruction of smaller fragments or stones, and accumulations of smaller objects.

According to the present invention an ultrasonic shock wave transducer for use in lithotripsy, hyperthermia and the like, for generating ultrasonic shock waves and transmitting them to a concretion or tissue to be destroyed, focuses the energy of the ultrasonic shock waves in proportion on at least two points disposed on a line situated around its main axis and at a distance from its radiating surface and being arbitrarily curved in three dimensions.

The accuracy of aiming of the shock waves is thus improved by deliberately increasing the focal area.

Theoretically, of course, the focal area could be increased simply by reducing the aperture of a known transducer. In this case, however, the energy density of the ultrasonic shock waves is increased at the surface of entry into the patient's body, thus causing pain. The increase in the focal area in the plane of radiation of the waves will also cause an increase in the spatial depth thereof, so that the energy in this region will not be distributed amongst the areas desired.

An ultrasonic shock wave transducer according to the invention can concentrate the ultrasonic energy on at least two points disposed on the line having any selected arbitrary curvature in three dimensions. The disadvantages of the theoretical solution discussed above are thereby avoided.

In one embodiment of the invention the transducer focuses the energy of the ultrasonic shock waves on to an infinite number of points, forming a continuous line curved in three dimensions.

If the curved line chosen is a circle, the focal area is annular.

Substantially any planar and substantially cap-shaped transducer can be arranged so that it operates as described above.

According to another embodiment the transducer, which generates ultrasonic shock waves and itself directs them against the concretion or tissue to be destroyed, is axially symmetrical and is dish-shaped as seen in cross-section with a diffusely reflecting base. In this case the focal area is a circle.

According to another embodiment of the invention, the transducer, which produces ultrasonic shock waves and itself directs them against the concretion or tissue to be destroyed, is made up of a plurality of segments each having a focus lying on the imaginary arbitrarily-curved line. If the individual segments are segments of a spherical cap, the individual foci of the segments will lie on an imaginary circle about the main axis of the transducer.

According to a further development of this embodiment, the individual segments are movable in translation in a plane relative to the main axis of the transducer. If, as before, the individual segments are cap segments, the diameter of the circle on which the individual foci lie will increase if all the individual segments are moved apart to the same extent. Said diameter will correspondingly decrease if the individual segments are moved together to the same extent, without overlapping. Even overlapping of individual sound cones is possible.

The line having an arbitrary curvature but which is predetermined by the specific shape of the transducer, can be adjusted by arranging the individual segments to be pivotable through an angle relative to the main axis of the transducer.

If the individual segments are cap segments, the diameter of the imaginary circle containing the individual foci will be increased if all the segments are pivoted through the same angle away from the main axis of the transducer.

According to another embodiment of the invention, an acoustic lens having a plurality of acoustic foci is disposed on the radiating surface of the transducer.

The lens may be a one-piece lens which is axially symmetrical, its thickness continuously increasing from the edge to the centre of the transducer, in which case the transducer will have an annular focal region.

In all of the embodiments described above, the cross-section of the focal area of the transducer in which area the energy density must be sufficient to destroy the concretion or tissue, is sufficiently large to allow of this.

Figure 1A:
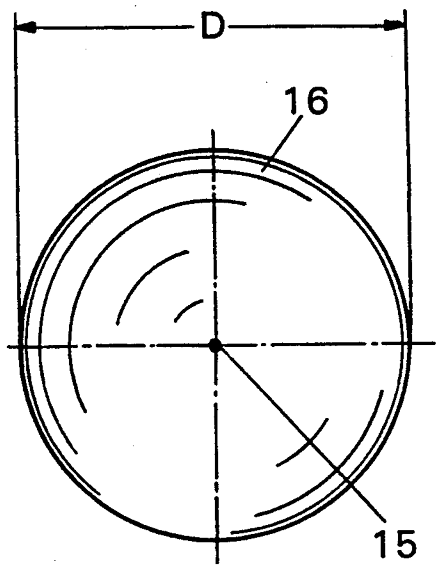
(PRIOR ART) Fig. 1a
FIGS. 1*a* and 1*b* are a plan view and a sectional view, respectively, of a known transducer.

All of the views shown in the drawings are diagrammatic.

DETAILED DESCRIPTION OF THE INVENTION

In order to produce ultrasonic shock waves, all of the embodiments illustrated can be equipped, for example, with a mosaic of piezoceramic elements (not shown).

In the drawings, like parts bear like reference numerals.

Figure 1C:
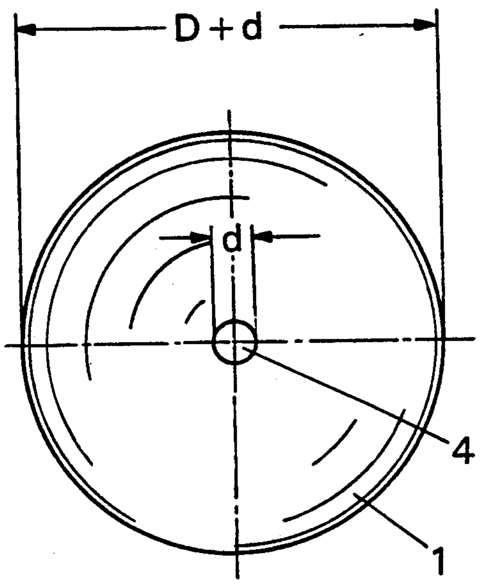
FIGS. 1*c* and 1*d* are a plan view and a sectional view, respectively, of a transducer according to a first embodiment of the invention.
Figure 1B:
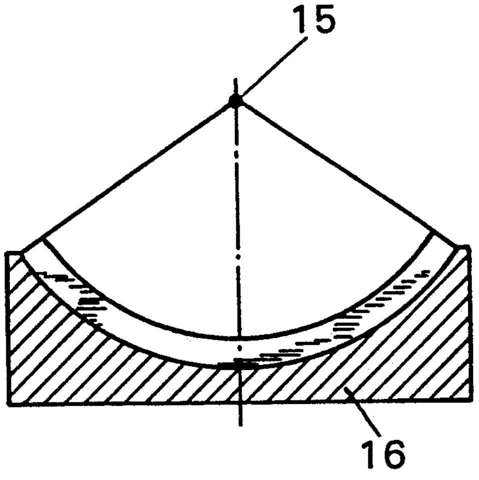
(PRIOR ART) Fig. 1b
Figure 1D:
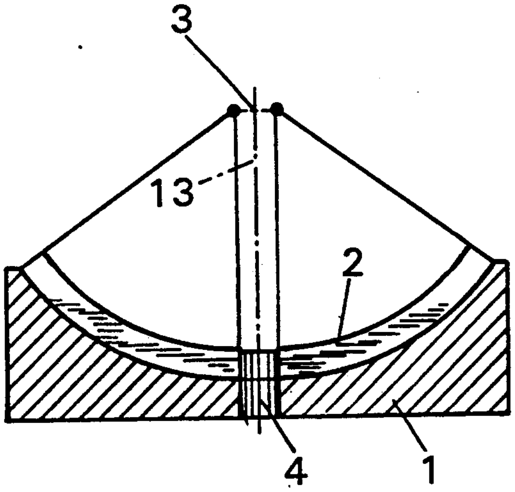

FIG. 1*a* is a plan view, and FIG. 1*b* is a cross-sectional view, of a known cap-shaped, self-focussing transducer 16, whereas FIGS. 1*c* and 1*d* are corresponding views of a transducer 1 according to a first embodiment of the invention.

The known transducer 16 has a focus 15, shown diagrammatically as a point, at which the ultrasonic shock waves are concentrated. During the application of the ultrasonic shock waves, the focus 15 is centered on an object to be destroyed, so that these coincide.

The transducer 1 is axially symmetrical and has a central planar base 4. In the region of the planar base 4, the transducer 1 has no transducer element, for example, piezoelectric elements such as those that are provided on its radiation surfaces 2. Transducer 1 delivers an axially symmetrical sound field. By virtue of its shape, the transducer 1 focuses the energy of the ultrasonic shock waves on to an infinite number of points situated on a continuous line 3 curved in three dimensions about its main axis 13. In the embodiment shown, the curved line 3 is a closed circle. The transducer 1, therefore, has a closed annular focal region.

Figure 2A:
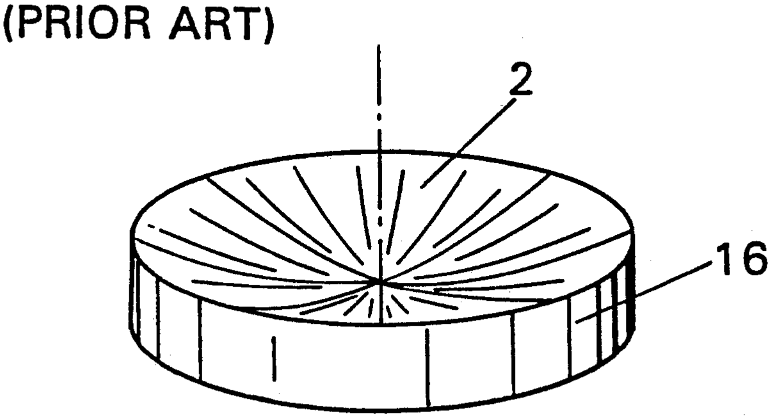
Fig. 2a (PRIOR ART)
FIG. 2*a* is an isometric view of the known cap transducer.
Figure 2B:
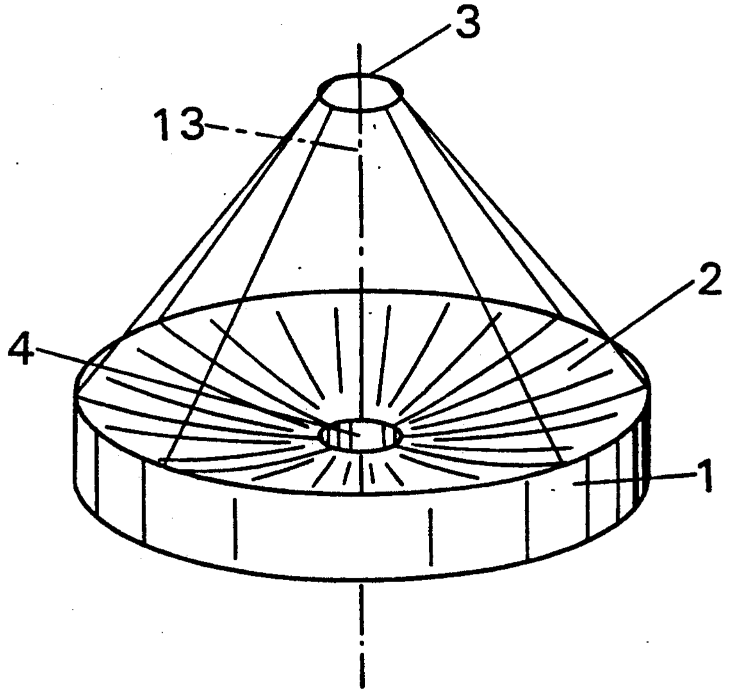
FIG. 2*b* is an isometric view of the transducer according to said first embodiment, and is arranged in axial alignment with FIG. 2*a*.

FIG. 2*a* is an isometric view of the known transducer 16 and FIG. 2*b* is an isometric view of the transducer 1, FIGS. 2*a* and 2*b* being axially aligned for the purpose of comparison. In FIGS. 2*a* and 2*b*, the curved lines within each transducer merely indicate the curvature of the radiation surfaces 2 thereof, and do not denote that the transducer is segmented.

Figure 3A:
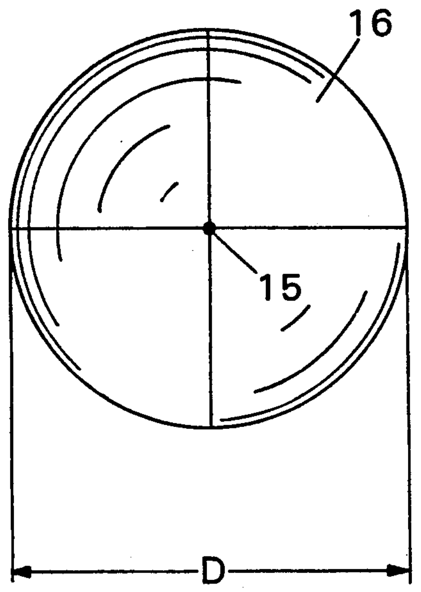
Fig. 3a (PRIOR ART)
FIGS. 3*a* and 3*b* are a plan view and a sectional view, respectively, of said known transducer.
Figure 3C:
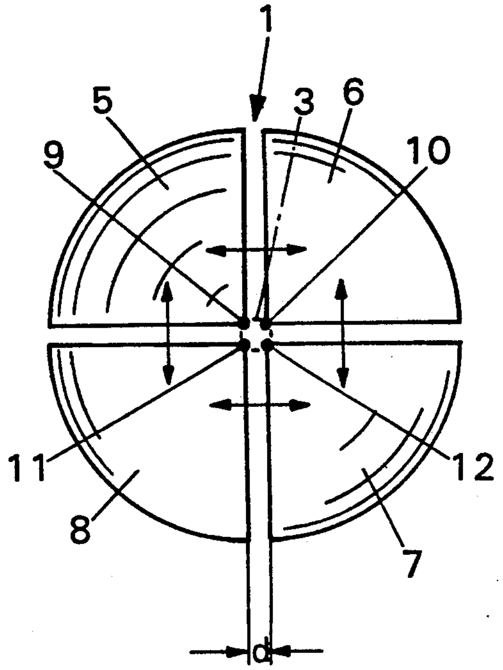
FIGS. 3*c* and 3*d* are a plan view and a sectional view, respectively, of a transducer according to a second embodiment of the invention.
Figure 3B:
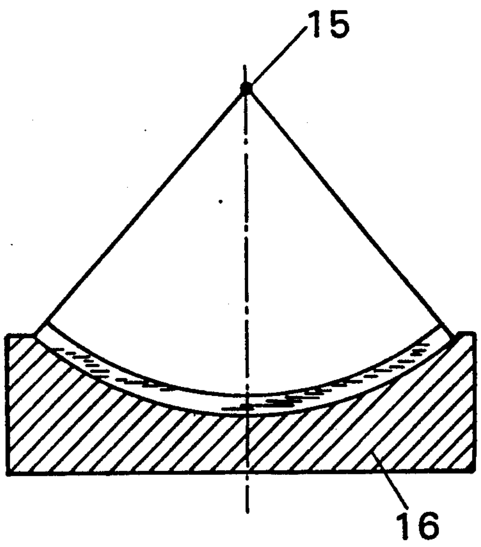
Fig. 3b (PRIOR ART)

In FIGS. 3*a* and 3*b* the known transducer 16 is similarly shown in comparison with a transducer 1 (FIGS. 3*c* and 3*d*) according to a second embodiment of the invention. The transducer 1 is divided into four segments 5, 6, 7 and 8. The segments 5, 6, 7 and 8 are cap-shaped, so that each has an individual focus 9, 10, 11 and 12, respectively. The segments 5, 6, 7, 8 are so disposed relative to one another that the individual foci 9, 10, 11, 12 lie on an imaginary curved line 3 in the form of a circle.

The individual segments 5, 6, 7 and 8 are movable in translation in a plane relative to the main axis 13 of the transducer 1, as indicated by double arrows in FIG. 3*c*. If, starting from the position shown, the individual segments are each moved by the same distance away from the main axis 13, the diameter of the imaginary circle 3 increases, said diameter becoming correspondingly smaller if the individual segments are each moved towards the main axis 13. This embodiment can be used to obtain other, non-circular lines corresponding to the line 3 if the distances through which the individual segments 5, 6, 7 and 8 are moved relative to the main axis 13 are unequal.

Figure 3D:
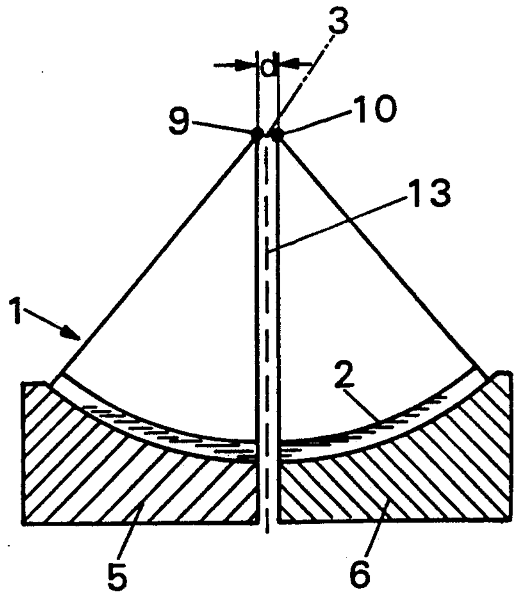
Figure 4A:
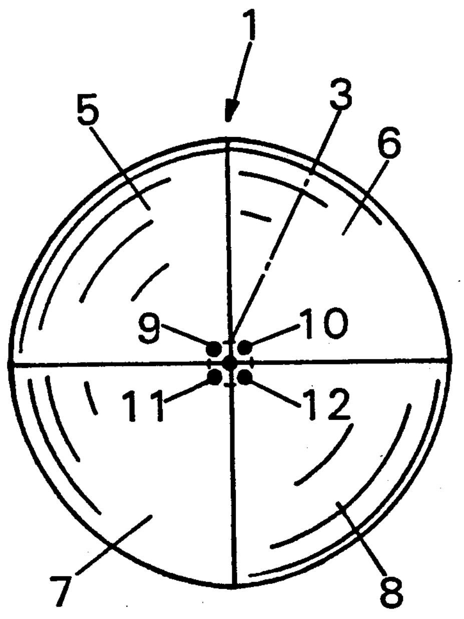
FIGS. 4*a* and 4*b* are plan views of a transducer according to a third embodiment of the invention, showing the transducer in a retracted condition and in an expanded condition, respectively.
Figure 4B:
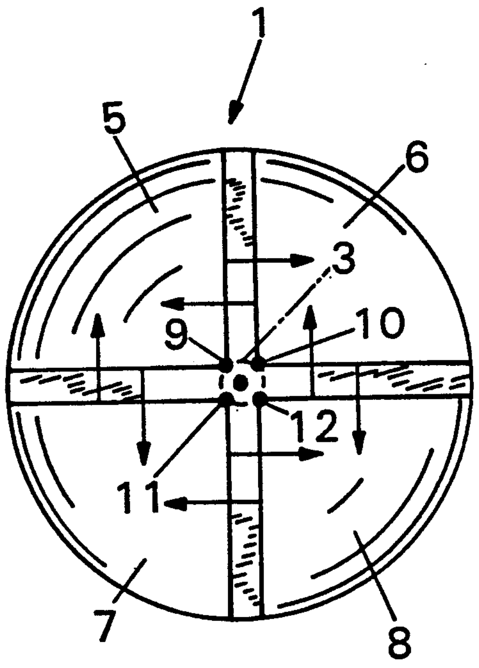

A transducer 1 according to a third embodiment of the invention (FIGS. 4*a* and 4*b*) is axially unsymmetrical. In contrast to the transducer 1 as shown in FIGS. 3*c* and 3*d* the transducer 1 shown in FIGS. 4*a* and 4*b* has a circular outer contour in its maximum extended position (FIG. 4*b*) whereas in the case of the transducer 1 of FIGS. 3*c* and 3*d* its outer contour is circular only when all the individual segments 5, 6, 7 and 8 have been moved to a maximum extent towards the main axis 13, when the transducer 1 (of FIGS. 3*c* and 3*d*) is basically in the position in which the transducer 16 is shown in FIG. 3*a*.

Figure 5B:
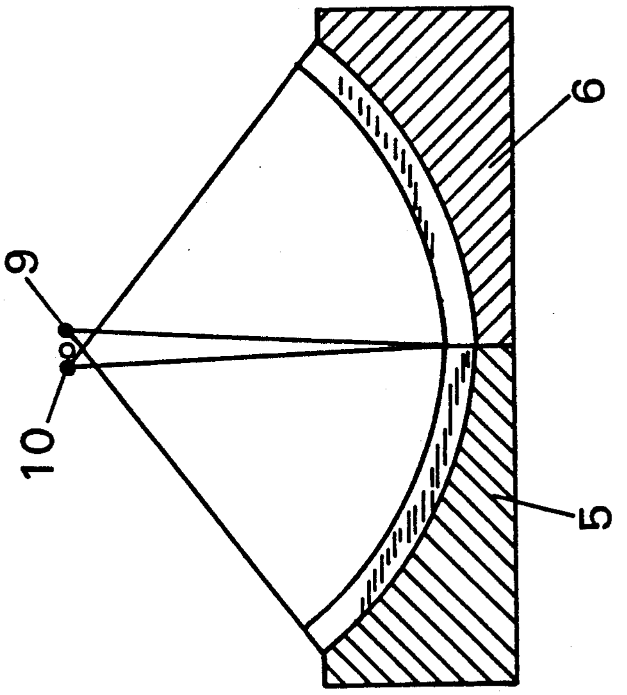
FIGS. 5*a* and 5*b* are sectional views of a transducer according to a fourth embodiment of the invention showing the transducer in a first condition and in a second condition, respectively.
Figure 5A:
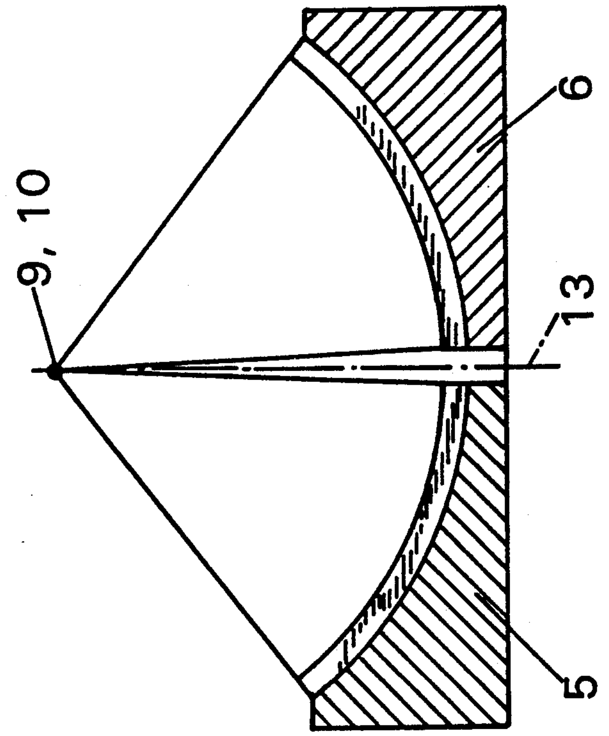

In the fourth embodiment, shown in FIGS. 5*a* and 5*b*, cap segments 5 and 6 are separated by a certain distance at their base in the position of FIGS. 5*a*. In this position the individual foci 9 and 10 coincide. Starting from that position, the individual segments 5 and 6 can be moved towards the main axis 13. The end position shown in FIG. 5*b* is reached if segments 5 and 6 both touch the main axis 13. In that position the sound cones proceeding from the individual segments 5 and 6 overlap, so that the individual foci 9 and 10 move apart. The segments 5 and 6 can, of course, be placed in any desired intermediate position between the positions shown in FIGS. 5*a* and 5*b*.

Figure 6A:
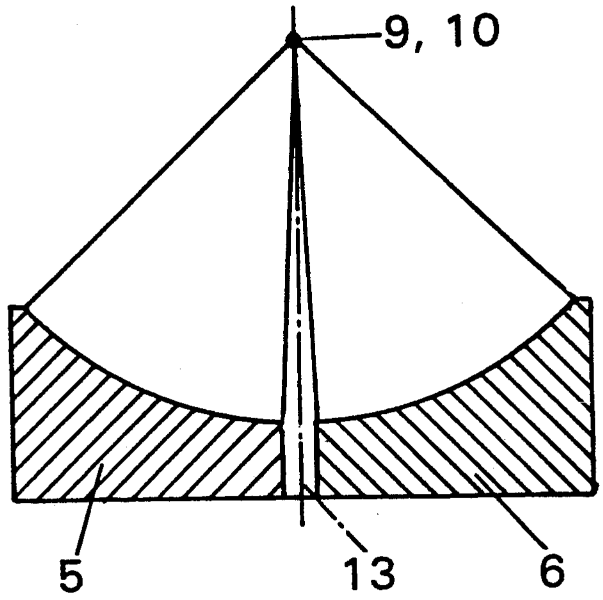
FIGS. 6*a* and 6*b* are sectional views of a transducer according to a fifth embodiment of the invention, showing the transducer in a first condition and in a second condition, respectively.
Figure 6B:
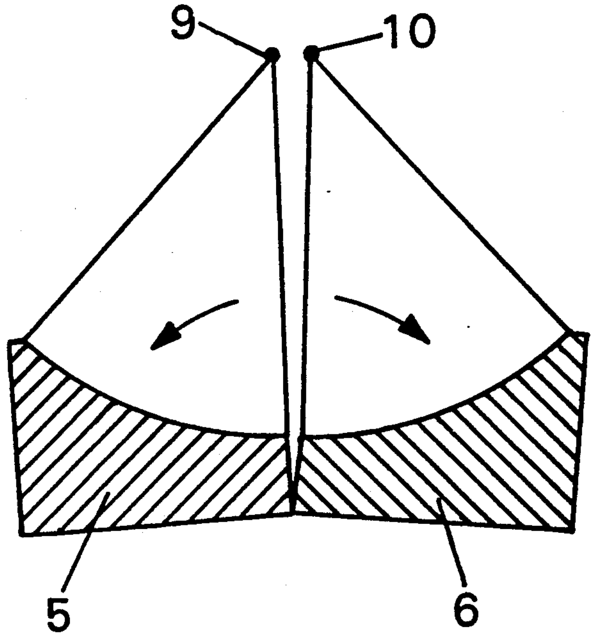

FIGS. 6*a* and 6*b* show a transducer according to a fifth embodiment of the invention. Segments 5 and 6 are pivotable through an angle relative to the main axis 13. Starting from an extreme position (FIG. 6*a*), in which the individual foci 9 and 10 coincide, the segments 5 and 6 can be pivoted for example into the position shown in FIG. 6*b* whereby the individual foci 9 and 10 are moved apart. The individual angles through which the individual segments 5 and 6 are pivoted need not, of course, always be equal. By varying the pivotal angle, the individual foci may be situated on variously curved lines instead of on a circle.

Figure 7A:
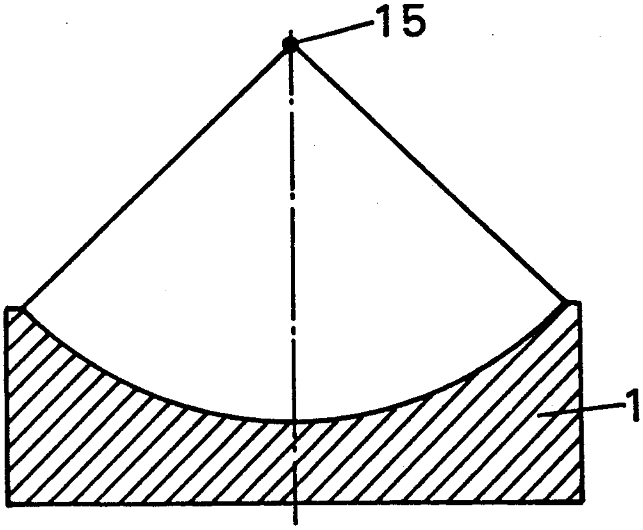
Fig. 7a (PRIOR ART)
FIG. 7*a* is a sectional view of a known transducer.
Figure 7B:
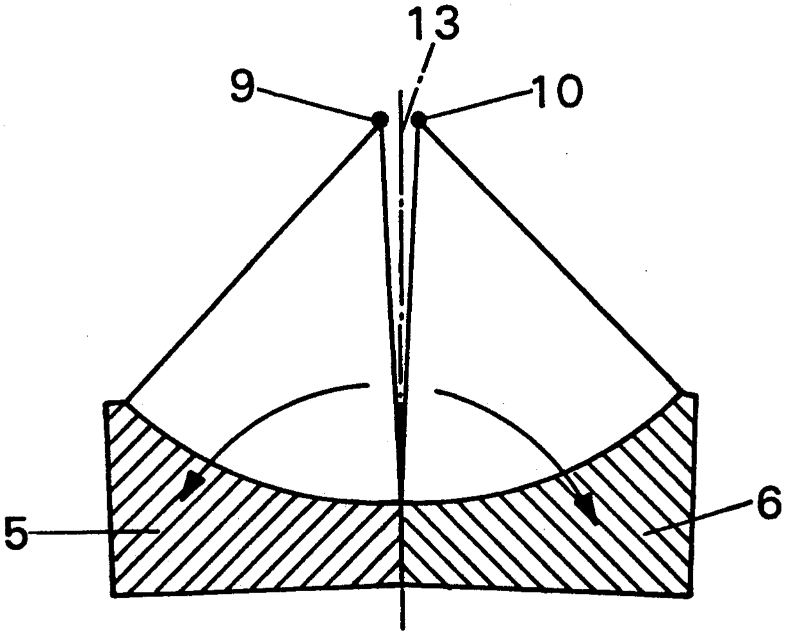
FIG. 7*b* is a sectional view of a transducer according to a sixth embodiment of the invention.

FIGS. 7*a* shows a known cap-shaped transducer 16 having a focus 15 for comparison with a transducer according to a sixth embodiment of the invention, which is shown in FIG. 7*b*. The transducer of FIG. 7*b* comprises a single axially symmetrical body obtained by tilting half-sections 5 and 6, and has an annular focus.

Figure 8:
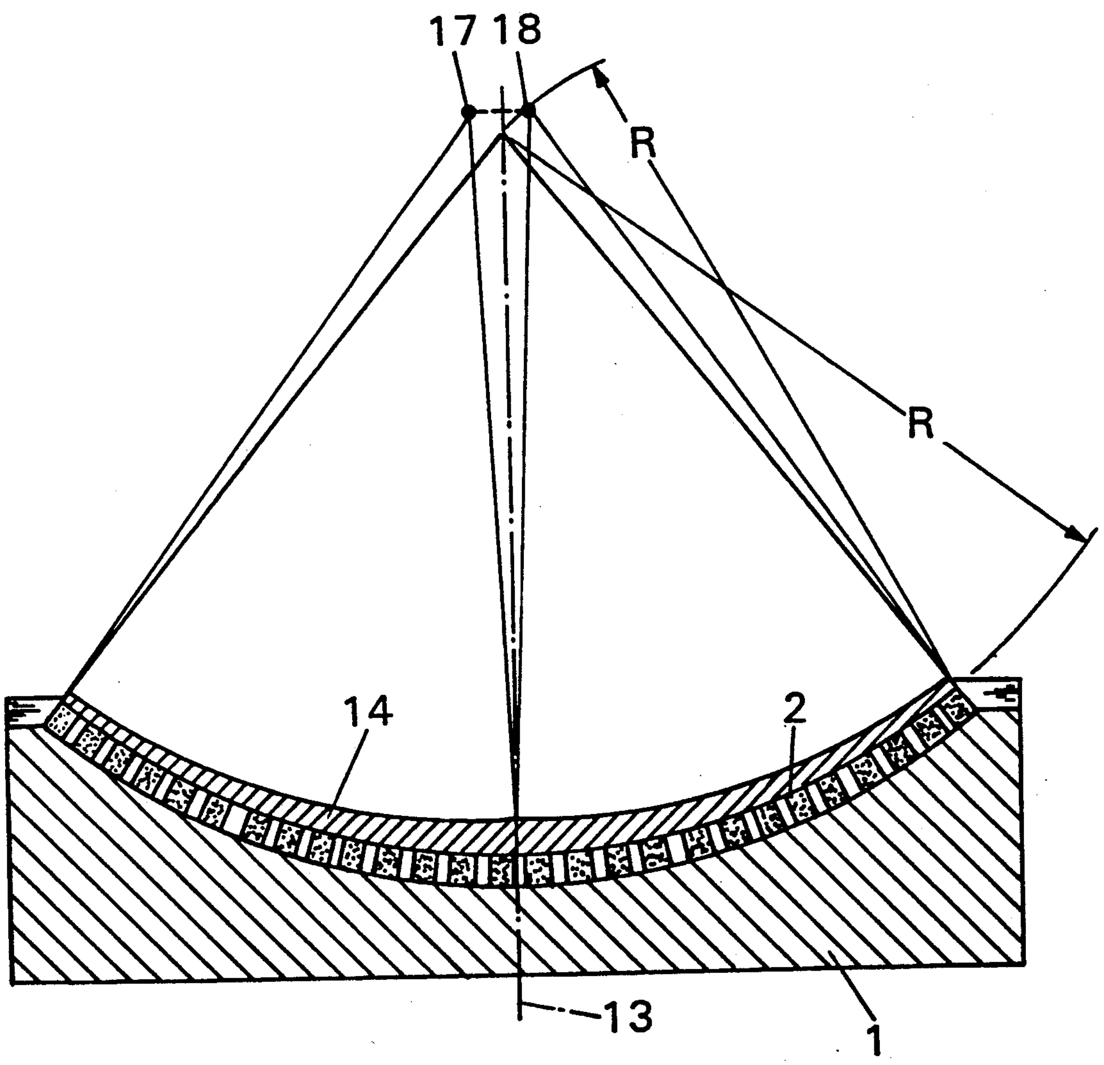
FIG. 8 is a sectional view of a transducer according to a seventh embodiment of the invention.

FIG. 8 shows a transducer 1 according to a seventh embodiment of the invention. An acoustic lens 14 disposed on the radiation surface 2 of the transducer 1 has a plurality of foci 17 and 18, whereby the focal area is not increased by moving or pivoting individual elements relative to the main axis 13, but by "acoustic tilting". The lens 14 is made in one piece and is axially symmetrical, the thickness of the lens 14 increasing continuously from the edge to the centre of the transducer 1. The transducer 1 has a focal area which lies on a curved line in the form of a closed circle. The diameter of the closed circle can be varied, thus varying the diameter of the annular focal area, in dependence upon the thickness of the lens 14 at the middle of the transducer and the speed of sound through the material thereof.

What is claimed is:

1. An ultrasonic shock wave transducer device for generating ultrasonic waves and transmitting them to an object to be destroyed, comprising a transducer having a cap-shaped radiating surface for generating ultrasonic shock waves and a main axis, and means located on said transducer for geometrically focussing the energy of said shock waves proportionately on at least two points disposed on a line which is arbitrarily curved about said main axis in three dimensions and is spaced from said radiating surface.

2. A transducer device as claimed in claim 1, wherein said at least two points comprise an infinite number of points forming a continuous line which is said curved line in three dimensions.

3. A transducer device as claimed in claim 2, wherein the radiating surface is so shaped as to direct said ultrasonic shock waves towards said object to be destroyed, and wherein said focussing means comprises said transducer being axially symmetrical and having a base so shaped that sound waves reflected thereat cannot meet in phase at the focus.

4. A transducer device as claimed in claim 1, wherein the radiating surface is so shaped as to direct said shock waves against said object to be destroyed, and wherein said focussing means comprises said radiating surface comprising a plurality of individual segments each having a focus which lies on an imaginary line which is said arbitrarily curved line in three dimensions.

5. A transducer device as claimed in claim 4, wherein the individual segments are movable in a plane transverse to said main axis.

6. A transducer device as claimed in claim 4, wherein said segments are pivotally movable through an angle relative to said main axis.

7. A transducer device as claimed in claim 1, wherein said focussing means comprises a lens having a plurality of acoustic foci, said lens being disposed on the radiating surface of the transducer.

8. A transducer device as claimed in claim 7, wherein said lens is a one-piece axially symmetrical lens having an outer edge and a center, the center being disposed at the main axis of the transducer, and wherein the thickness of the lens increases continuously from the outer edge to the center.

* * * * *